US009147825B2

(12) United States Patent
Kim et al.

(10) Patent No.: US 9,147,825 B2
(45) Date of Patent: Sep. 29, 2015

(54) METHODS OF FABRICATING MULTI-DEGREE OF FREEDOM SHAPED ELECTROACTIVE POLYMER ACTUATORS/SENSORS FOR CATHETERS

(71) Applicant: The Board of Regents of the Nevada System of Higher Education, on Behalf of the University of Nevada, Reno, NV (US)

(72) Inventors: Kwang J. Kim, Henderson, NV (US); Seong Jun Kim, Reno, NV (US); Johnson Wong, Reno, NV (US)

(73) Assignee: Board of Regents of the Nevada System of Higher Education on behalf of the University of Nevado, Reno, Reno, NV (US)

( * ) Notice: Subject to any disclaimer, the term of this patent is extended or adjusted under 35 U.S.C. 154(b) by 336 days.

(21) Appl. No.: 13/787,587

(22) Filed: Mar. 6, 2013

(65) Prior Publication Data
US 2013/0253424 A1   Sep. 26, 2013

Related U.S. Application Data

(60) Provisional application No. 61/608,043, filed on Mar. 7, 2012.

(51) Int. Cl.
*H01L 41/09* (2006.01)
*H01L 41/22* (2013.01)
(Continued)

(52) U.S. Cl.
CPC .............. *H01L 41/047* (2013.01); *F03G 7/00* (2013.01); *H01L 41/29* (2013.01); *A61M 25/0158* (2013.01); *A61M 2025/0058* (2013.01); *Y10T 29/42* (2015.01)

(58) Field of Classification Search
USPC ................ 310/309, 311, 328, 365–367, 800; 29/25.35
See application file for complete search history.

(56) References Cited

U.S. PATENT DOCUMENTS 6,376,971 B1   4/2002  Pelrine et al.
6,812,624 B1 * 11/2004  Pei et al. ...................... 310/309
(Continued)

FOREIGN PATENT DOCUMENTS

WO   WO 2007/101448   9/2007
WO   WO 2008/054577   5/2008

OTHER PUBLICATIONS

Biddiss et al., "Electroactive polymeric sensors in hand prostheses: Bending response of an ionic polymer metal composite," *Medical Engineering and Physics*, vol. 28, No. 6, pp. 568, Jul. 2006.
(Continued)

*Primary Examiner* — Thomas Dougherty
(74) *Attorney, Agent, or Firm* — Klarquist Sparkman, LLP

(57) ABSTRACT

Disclosed is a method of fabricating a multiple degree of freedom actuator with inter-digitated electrodes including molding an electroactive polymer membrane so that a plurality of projections are formed around a cross section of an outer surface of the polymer membrane; depositing a metal electrode layer onto the outer surface of the molded membrane; and removing the plurality of projections on the outer surface on the molded membrane, thereby forming a multiple degree of freedom actuator with a plurality of inter-digitated electrodes. Also provided are actuators as well as devices (such as catheters) including such actuators formed by the disclosed methods of fabricating an actuator with multiple DOF.

18 Claims, 19 Drawing Sheets

(51) Int. Cl.
   *H01L 41/047* (2006.01)
   *H01L 41/29* (2013.01)
   *F03G 7/00* (2006.01)
   *A61M 25/01* (2006.01)
   *A61M 25/00* (2006.01)

(56) References Cited

U.S. PATENT DOCUMENTS

| | | | |
|---|---|---|---|
| 6,940,211 B2 | 9/2005 | Pelrine et al. | |
| 7,038,357 B2 | 5/2006 | Goldenberg et al. | |
| 8,395,300 B2* | 3/2013 | Aabloo et al. | 310/328 |
| 8,398,693 B2 | 3/2013 | Weber et al. | |
| 2003/0006669 A1 | 1/2003 | Pei et al. | |
| 2004/0217671 A1* | 11/2004 | Rosenthal et al. | 310/328 |
| 2007/0257582 A1* | 11/2007 | Yokoyama et al. | 310/800 |
| 2009/0027833 A1 | 1/2009 | Lee et al. | |
| 2009/0130423 A1* | 5/2009 | Keady | 428/304.4 |
| 2010/0055378 A1 | 3/2010 | Kim et al. | |

OTHER PUBLICATIONS

Bonomo et al., "A tactile sensor for biomedical applications based on IPMCs," *IEEE Sensors Journal*, vol. 8, No. 8, pp. 1486-1493, Aug. 2008.

Chen et al., "Modeling of Biomimetic Robotic Fish Propelled by an Ionic Polymer-Metal Composite Caudal Fin," *Mechatronics, IEEE/ASME Transactions on*, vol. 15, No. 3, pp. 448-459, 2010.

Fang et al., "A new approach to develop ionic polymer—metal composites (IPMC) actuator: Fabrication and control for active catheter systems," *Sensors & Actuators A: Physical*, vol. 137, No. 2, pp. 321-329, 2007.

Kim et al., "A biomimetic undulatory tadpole robot using ionic polymer—metal composite actuators," *Smart Materials and Structures*, vol. 14, No. 6, pp. 1579, 2005.

Mazzoldi et al., "Conductive-polymer-based structures for a steerable catheter." *Proc. SPIE*, 3987, pp. 273 (2000).

Mbemmo et al., "Modeling of biomimetic robotic fish propelled by an ionic polymer-metal composite actuator." pp. 689-694.

Shahinpoor et al., "Ionic polymer-metal composites (IPMCs) as biomimetic sensors, actuators and artificial muscles—a review," *Smart Materials and Structures*, vol. 7, No. 6, pp. R15, Dec. 1998.

Shahinpoor et al., "Ionic polymer-metal composites: I. Fundamentals," *Smart Materials & Structures*, vol. 10, No. 4, pp. 819-833, 2001.

Shahinpoor et al., "Ionic polymer—metal composites: IV. Industrial and medical applications," *Smart Materials and Structures*, vol. 14, No. 1, pp. 197, 2005.

Shahinpoor, "Ionic polymer—metal composites: III. Modeling and simulation as biomimetic sensors, actuators, transducers, and artificial muscles," *Smart Materials and Structures*, vol. 13, No. 6, pp. 1362, 2004.

Shahinpoor et al., "Ionic Polymer-Metal Composites (IPMC) as Biomimetic Sensors and Actuators-Artificial Muscles", *Proceedings of SPIE's 5th Annual International Symposium on Smart Structures and Materials*, Mar. 1-5, 1998, San Diego, CA. pp. 3324-3327.

Yoon et al., "Analysis of electro-active polymer bending: A component in a low cost ultrathin scanning endoscope," *Sensors and Actuators A: Physical*, vol. 123, No. 2, pp. 506-517, 2007.

* cited by examiner

METHODS OF FABRICATING MULTI-DEGREE OF FREEDOM SHAPED ELECTROACTIVE POLYMER ACTUATORS/SENSORS FOR CATHETERS

CROSS REFERENCE TO RELATED APPLICATION

This application claims the benefit of U.S. Provisional Application No. 61/608,043, filed Mar. 7, 2012, which is herein incorporated by reference in its entirety.

ACKNOWLEDGMENT OF GOVERNMENT SUPPORT

This invention was made with government support under grant number CNS0958568 awarded by the National Science Foundation and grant number N000140910218 awarded by the Office of Naval Research. The government has certain rights in the invention.

FIELD

This disclosure concerns electroactive composites, and in particular, methods of fabricating multi-degree of freedom shaped electroactive polymer actuators/sensors, and actuators/sensors formed thereof, such as used in catheters.

BACKGROUND

IPMC (ionic polymer-metal composite) is a subset of electroactive polymer (EAP) and is, in general, composed of an ionic polymer membrane and conductive electrode layers on the surfaces of the membrane. Typically, IPMCs are made to have thin beam shapes and exhibit a simple bending actuation. To achieve the multi-degrees of freedom (DOF) actuation, the surface electrode layer of the rod-shaped IPMC should be inter-digitated to have multiple electrically insulated sections. Then, it can bend to multiple directions by applying selective electrical signals on the electrode sections. Existing techniques for electrode inter-digitation are mechanical or laser machining which require complicated and expensive equipment. For convenient and inexpensive inter-digitation of the electrode, the ionic polymer membrane needs to be molded to have multiple (the number of inter-digitation) small bumps around the cross-section. After depositing the electrode layer on the surface of the molded membrane or rod, the electrode layer can be easily inter-digitated by eliminating the bumps with a simple cutting tool.

SUMMARY

Ionic polymer-metal composite (IPMC) material is one of the most promising active (smart) material for developing novel soft biomimetic actuators and sensors. The advantages of the IPMC include low driving voltage (<5 V), relatively large strain, soft and flexible structure, and the ability to operate in an aqueous environment (such as water or blood). Due to the softness and flexibility of the material, it can be used to mimic the muscle-like behavior as seen in the nature. For instance, a number of robotic applications based on the IPMCs have been proposed. Among others, the list includes an active fish fin for propulsion, jellyfish based on the soft materials. Furthermore, due to the bio-compatibility the IPMCs are promising materials in the biomedical field.

Whereas the flat, beam-shaped IPMCs have been extensively studied for different applications, cylindrical IPMCs have not yet been investigated. This is primarily due to the difficulties related to the fabrication process and a small deflection angle which is mainly caused by the high mechanical rigidity. However, the cylindrical IPMC is a promising candidate to be used as, for instance, an active catheter platform if it can show two degrees of freedom (2-DOF) actuation capability. The inventors disclose herein the surprising discovery that cylindrical IPMCs can achieve 2-DOF actuation capability by inter-digitating the surface electrodes and applying appropriate combinations of input signals as illustrated in FIG. 1.

Based upon these findings, disclosed herein are methods of fabricating an actuator with multiple DOF. In some embodiments, a method of fabricating a multiple degree of freedom actuator with inter-digitated electrodes, comprises molding an electroactive polymer membrane so that a plurality of projections are formed around a cross section of an outer surface of the polymer membrane; depositing a metal electrode layer onto the outer surface of the molded membrane; and removing the plurality of projections on the outer surface on the molded membrane, thereby forming a multiple degree of freedom actuator with a plurality of inter-digitated electrodes.

The present disclosure also provides actuators formed by the disclosed methods of fabricating an actuator with multiple DOF. The fabricated actuators convert electrical energy into mechanical energy. In some embodiments, a disclosed actuator comprises an electroactive polymer, such as an ionic polymer including ionic-polymer-metal composite (IPMC) material with a plurality of electrically insulated sections formed by inter-digitation. In some examples, the actuator is cylindrical in shape and includes 4 electrically insulated sections (also referred to as inter-digitated electrodes) resulting in actuation capability in 4 directions. In some embodiments, the actuator further includes a contact electrode. In some examples, the contact electrode is connected to the inter-digitated electrodes by a composition comprising conductive silicone rubber.

The disclosed methods and actuators/sensors produced therefrom can be used in various devices, including various medical devices. In some embodiments, one or more of the disclosed actuators is used in a catheter or a component of a catheter.

The foregoing and other features and advantages of the disclosure will become more apparent from the following detailed description, which proceeds with reference to the accompanying figures.

DETAILED DESCRIPTION OF SEVERAL EMBODIMENTS

Figure 1A:
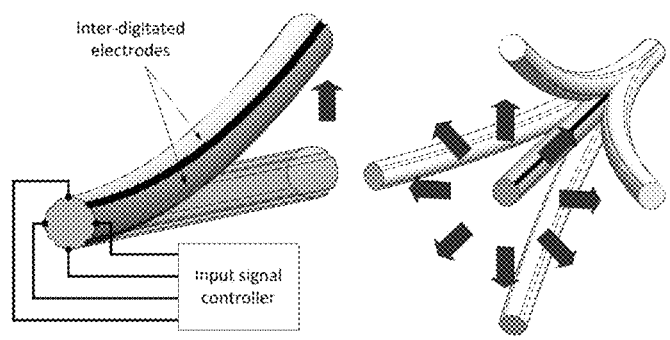
FIG. 1A is a schematic drawing of a cylindrical IPMC with four inter-digitated electrodes (left) and illustrated actuation (right).
Figure 1B:
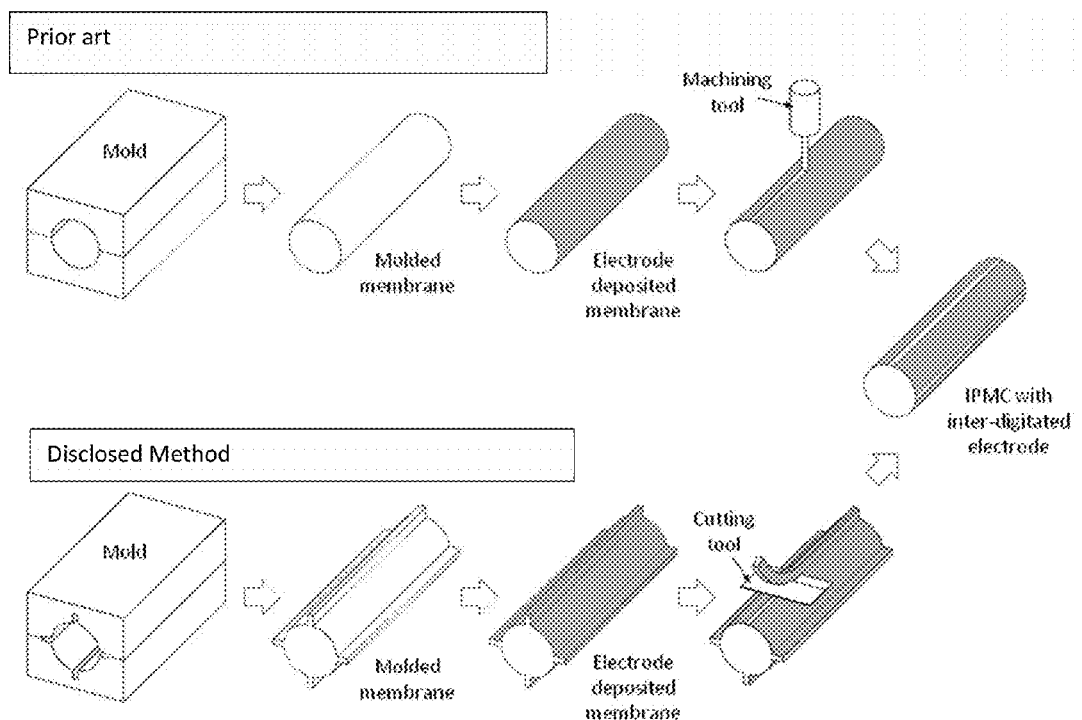
FIG. 1B is a schematic drawing illustrating one example of the existing (prior art, top panel) and disclosed (bottom panel) electrode inter-digitating processes.

The following description is exemplary in nature and is not intended to limit the scope, applicability, or configuration of the disclosure in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernible, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

I. Methods of Fabricating a Multiple Degree of Freedom Actuator

Disclosed herein are methods of fabricating a multiple degree of freedom actuator. In some embodiments, the method includes molding a polymer membrane so that a plurality of projections are formed around a cross section of an outer surface of the polymer membrane; depositing a metal electrode layer onto the outer surface of the molded membrane; and removing the plurality of projections on the outer surface on the molded membrane, thereby forming a multiple degree of freedom actuator with a plurality of inter-digitated electrodes.

It is contemplated that the membrane including a plurality of projections may be formed of any polymer with the desired properties known to one of ordinary skill in the art. In some embodiments, the membrane is formed of an electroactive polymer (EAP). Electroactive polymers are polymers characterized by their ability to change shape in response to electrical stimulation. Electroactive polymers (EAPs) are discussed in detail in U.S. patent application Ser. No. 10/763,825, the entire content of which is incorporated by reference herein.

Two principal classes of EAPs are dielectric and ionic. Ionic EAP is a type of EAP, in which actuation is caused by the displacement of ions inside the polymer. A major advantage of ionic EAPs is that they require only a few volts for actuation, but the resultant ionic flow implies a higher electrical power and energy needed to keep the actuator at a given position. Conductive polymers, ionic polymer-metal composites (IPMCs), and responsive gel are examples of ionic EAPs.

The electroactive polymers that are typically used in connection with the present disclosure are ionic EAPs, more typically those EAPs that feature an ion-exchange capable polymer network or a conjugated backbone and have the ability to increase electrical conductivity under oxidation or reduction. In some examples, the membranes comprise ionic EAPs, such as one with a perfluorinated ionomer backbone (e.g., Nafion® or Flemion®). Some commonly known ionic EAPs are polypyrrole, polyaniline, polythiophenes, polyethylenedioxythiophene, poly(p-phenylene vinylene), polysulfone and polyacetylene. These EAPs are typically semi-conductors in their pure form. However, upon oxidation or reduction of the polymer, the electrical conductivity is understood to be changed from a semi-conductive regime to a semi-metallic regime. Such oxidation and reduction is believed to lead to a charge imbalance that, in turn, results in a flow of ions into or out of the material. These ions typically enter/exit the polymer from/into an ionically conductive electrolyte medium associated with the electroactive polymer.

It is well known that dimensional changes are effectuated in certain polymers by the mass transfer of ions into or out of the polymer. For example, in some polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses and strains. These characteristics are desirable for construction of the devices of the present disclosure. As used herein, active member "actuation" refers to either the expansion or the contraction of the active member.

Conductive EAPs also have a number of additional properties that make them attractive for use in the devices of the present disclosure, including the following: (a) they are lightweight, flexible, and easily manufactured; (b) small changes in potential (e.g., potential changes on the order of 1V) can be used to effect volume change; (c)

EAP regions can be created using a variety of techniques, for example, electrodeposition; and (d) EAP regions can be patterned, for example, using photolithography, if desired.

It is contemplated that the membrane may be molded by any method known to one of skill in the art, including hot-pressed in a mold of a desired shape, solution cast in a mold of a desirable shape, and 3-D printed of a desirable shape. It is further contemplated that the shape of the membrane may vary depending upon the desired use. In some examples, the membrane is substantially cylindrical, rectangular, circular, or flat, beam-shaped, and any other 3 dimensional shapes. In one example, the membrane is substantially cylindrical. The term substantially reflects the presence of at least one, such as at least two, at least three, at least four, at least five, at least six, at least seven or more, including one, two, three, four, five, six, seven, eight, ten troughs positioned along the body of membrane mold which allow for the at least one projection to be formed on the body of the membrane. The diameter of the membrane body may vary as desired. In some examples, the membrane mold is designed to form a membrane body with a diameter of at least 0.25 mm, such as between 0.25 mm and 0.5 mm, between 0.5 mm and 10 mm, such as between 0.5 mm and 5 mm, between 1 mm and 3 mm, including 0.5 mm, 0.6 mm, 0.7 mm, 0.8 mm, 0.9 mm, 1.0 mm, 1.2 mm, 1.5 mm, 1.8 mm, 2.0 mm, 2.2 mm, 2.5 mm, 3.0 mm, 4.0 mm, 5.0 mm, 6.0 mm, 7.0 mm, 8.0 mm, 9 mm, or 10 mm. The membrane mold may also be designed to form membranes with bodies that vary in length. For example, the membrane mold may be designed to form a membrane body with a length of at least 0.1 mm, such as a length between 0.1 mm and 20 mm In some examples, the mold is designed to include one or more troughs which are positioned equal distance to one another around the body of the membrane. For example, a membrane including 4 projections equal distant to one another is formed by using a membrane mold including troughs which are position about 90° from one another around the center of the membrane body. The depth, width and length of the trough may vary depending upon the desired size of the resulting projection. In some non-limiting examples, the trough depth varies from 0.1 mm and 2 mm. In some non-limiting examples, the trough width varies from about 0.1 mm to about 10 mm, such as between 2 mm and 8 mm, 2 mm and 4 mm, including 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm. In some non-limiting examples, the length of the trough is the equivalent to the length of the body of the membrane. For example, a mold designed to form a membrane body of about 20 mm in length may include one or more troughs of about 20 mm in length. In other non-limiting examples, the length of the trough is less than the length of the body of the membrane.

It is further contemplated that the membrane mold may be designed to generate projections with of varying shape, including, but not limited to, sharp edges, smooth edges, jagged edges or a combination thereof. In some embodiments, the trough within the membrane is designed to form projections with sharp edges. In some embodiments, the trough with the membrane is designed to form projections with smooth edges.

Following molding a polymer membrane including one or more projections around the outer surface of the membrane, the disclosed method of fabrication includes depositing a metal electrode layer onto the outer surface of a molded membrane. Any method of deposition known to one of ordinary skill in the art may be used to deposit a metal electrode layer onto the outer surface of a molded membrane. In some examples, the planar surfaces of the molded membrane are coated with conductors, such as platinum or gold or conducting polymers or conducting ceramics. In one example, a platinum electrode layer is deposited, such as chemically deposited, onto the outer surface layers of the molded membrane.

The disclosed method of fabrication further includes removing the plurality of projections on the outer surface on the molded membrane, such as with a simple cutting tool. In one example, a razor blade is used to remove the plurality of projections. Cutting tools like high-speed drills, sharp knives, lasers, heated tips, and others can be also used. In some examples, removing the plurality of projections on the outer surface on the molded membrane does not include mechanical or laser machining.

In some examples, a disclosed method of fabrication includes an activation process which follows the molding process, but is prior to depositing a metal electrode layer onto the outer surface of the molded membrane. In one example, an activation process includes hydrolyzing the membrane and then converting the cations of the hydrolyzed membrane to $H^+$ form. This process may be desired to be performed on membranes formed of polymers which do not have the desired cation-exchange properties.

In one particular example, a disclosed method of fabrication includes molding an ionic polymer (such as Nafion®) into a membrane with a plurality of projections, such as with a membrane mold with a cylindrical body and a plurality of troughs (such as 4) by use of a hot-press (such as hot pressing the ionic polymer in a mold at 3,000 psi for 30 minutes at an elevated temperature of 150° C.) so that a plurality of projections are formed around a cross section of an outer surface of the polymer membrane (such as at about 90° from each other). The method further includes activating the membrane so that it has the desired cation-exchange properties, such as by use of a two-step activation process including membrane hydrolysis and acid conversion. For example, the membrane is hydrolyzed in a solution of KOH at an elevated temperature. After the hydrolysis, the cations of the membrane are in $K^+$ form. The cations of the hydrolyzed membrane are then converted to $H^+$ form, such as by treating the hydrolyzed membrane with a 15% solution of $HNO_3$. The method further includes depositing a platinum electrode layer onto the outer surface of the activated cylindrical molded membrane, such as by use of a platinum electroless plating process. If desired, the cations of the fabricated cylindrical IPMC can be exchanged to $Li^+$ form following the depositing of the platinum electrode layer. The method includes removing the plurality of projections on the outer surface on the resulting membrane by a simple cutting tool (such as a razor blade), thereby forming a multiple degree of freedom actuator with a plurality of inter-digitated electrodes.

II. Actuator with Multiple Degrees of Freedom

The disclosed method of fabrication produces actuators with improved electroactive properties and which display artificial muscle behavior under an applied voltage. More specifically, under an applied voltage of (1-5V), ion migration and electrostatic repulsion result in a bending actuation. Furthermore, the resulting actuators, such as those comprising IPMC materials, can achieve a multi degree of freedom (DOF) of actuation. In some examples, to achieve the multi-DOF actuation, the surface electrode layer of the rod-shaped IPMC is inter-digitated to have multiple electrically insulated sections, so that it can be bend in multiple directions by applying selective electrical signals on the electrode sections.

In some examples, a disclosed actuator comprises an ionic EAPS, such as an ionic EAPS with a perfluorinated ionomer backbone (e.g., Nafion® or Flemion®). In some examples, a disclosed actuator comprises an EAPs are polypyrrole, polyaniline, polythiophenes, polyethylenedioxythiophene, poly(p-phenylene vinylene), polysulfone and polyacetylene It is contemplated that the shape of the membrane body of a disclosed actuator can vary depending upon the desired use. In some examples, the membrane body of the actuator is substantially cylindrical, rectangular, or flat, beam-shaped or ball-shaped. In one example, the membrane body is substantially cylindrical. The term substantially reflects the presence of at least one, such as at least two, at least three, at least four, at least five, at least six, at least seven or more, including one, two, three, four, five, six, seven, eight inter-digitations resulting in at least one, such as at least two, at least three, at least four, at least five, at least six, at least seven or more, including one, two, three, four, five, six, seven, eight, ten electrically insulated sections. The diameter of the membrane body may vary as desired. In some examples, the membrane body has a diameter of at least 0.1 mm, such as between 0.5 mm and 10 mm, such as between 0.5 mm and 5 mm, between 0.1 mm and 0.5 mm, between 1 mm and 3 mm, including 0.5 mm, 0.6 mm, 0.7 mm, 0.8 mm, 0.9 mm, 1.0 mm, 1.2 mm, 1.5 mm, 1.8 mm, 2.0 mm, 2.2 mm, 2.5 mm, 3.0 mm, 4.0 mm, 5.0 mm, 6.0 mm, 7.0 mm, 8.0 mm, 9 mm, or 10 mm. The length of the membrane body of the actuator varies depending upon the desired use. For example, the membrane body length is at least 0.1 mm, such as a length between 0.1 mm and 20 mm. In one particular example, the membrane body is about 20 mm in length.

In some examples, the actuator includes at least one or more electrically insulated sections formed by inter-digitation. In some examples, two or more electrically insulated sections formed by inter-digitation are positioned equal distance to one another around the body of the membrane. For example, 4 electrically insulated sections are equal distant to one another whereby they are positioned 90° from one another around the center of the membrane body. In some examples, two or more electrically insulated sections formed by inter-digitation are positioned at non-equal distances to one another around the body of the membrane.

The depth, width and length of each electrically insulated section may vary depending upon the desired use or properties. In some non-limiting examples, the depth varies from 0.1 mm and 10 mm. In some non-limiting examples, the electrically insulated section width varies from about 0.1 mm to about 10 mm, such as between 0.2 mm and 8 mm, 2 mm and 4 mm, including 0.1 mm, 0.2 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm. In some non-limiting examples, the length of the electrically insulated section is the equivalent to the length of the body of the membrane. For example, a section length is about 20 mm in length for a actuator with a membrane body of about 20 mm in length. In other non-limiting examples, the length of the section is less than the length of the body of the membrane.

In some examples, a disclosed actuator has the capability of bending to angles up to 90°, such as between about 10° and about 30°, about 30° and about 55°, about 40° and about 80°, including about 90°, about 89°, about 88°, about 87°, about 86°, about 85°, about 84°, about 83°, about 82°, about 81°, about 80°, about 79°, about 78°, about 77°, about 76°, about 75°, about 74°, about 73°, about 72°, about 71°, about 70°, about 69°, about 68°, about 67°, about 66°, about 65°, about 64°, about 63°, about 62°, about 61°, about 60°, about 59°, about 58°, about 57°, about 56°, about 55°, about 54°, about 53°, about 52°, about 51°, about 50°, about 49°, about 48°, about 47°, about 46°, about 45°, about 44°, about 43°, about 42°, about 41°, about 40°, about 39°, about 38°, about 37°, about 36°, about 35°, about 34°, about 33°, about 32°, about 31°, about 30°, about 29°, about 28°, about 27°, about 26°, about 25°, about 24°, about 23°, about 22°, about 21°, about 20°. In one example, a disclosed actuator has the capability of bending to angles up to 50°.

In some examples, a disclosed actuator further comprises one or more contact electrodes, such as one, two, three, four, five, six, seven, eight, or ten contact electrodes. In some examples, the one or more contact electrode is connected to the one or more inter-digitated electrically insulated section (also referred to as an inter-digitated electrode) by a composition comprising silicone rubber. For example, the one or more contact electrode is connected to the one or more inter-digitated electrode by silicone rubber tubing.

In further examples, a disclosed actuator further comprises at least one input signal controller, such as one, two, three, four, five, six, seven, eight, or ten input signal controllers, which controls the input signal from a secondary device or component.

III. Uses of the Disclosed Actuators

The present disclosure also relates to the use of one or more of the disclosed actuators in a device, such as a medical device. The actuators described herein may be used in any type of medical device, particularly those which are insertable and/or implantable within a body lumen. Specific examples of medical devices where the actuators described herein may be employed include catheter assemblies and components thereof which are employed for a variety of medical procedures. Catheters are widely used in medical applications, e.g., for intravenous, arterial, peritoneal, pleural, intrathecal, subdural, urological, synovial, gynecological, percutaneous, gastrointestinal, abscess drains, and subcutaneous applications. Catheters are placed for short-term, intermediate, and long-term usage. Examples of catheter assemblies include, but are not limited to, guide catheters, balloon catheters such as PTA and PTCA catheters for angioplasty, catheters for prostate therapy, TTS endoscopic catheters for gastrointestinal use, single operator exchange or rapid exchange (SOE or RX) catheters, over-the-wire (OTW) catheters, fixed wire catheters, medical device delivery catheters including stent delivery devices in both the self-expanding and balloon expandable varieties, catheters for delivery of vena cava filters, catheters for delivery of percutaneous patent foramen ovale (PFO) closure devices, therapeutic substance delivery devices, thrombectomy devices, endoscopic devices, angiographic catheters, neuro catheters, dilatation catheters, urinary tract catheters, gastrointestinal catheter devices, heat transfer catheters including thermal catheters and cooling, intravascular ultrasound systems, electrophysiology devices, and so on and so forth. The above list is intended for illustrative purposes only, and not as a limitation on the scope of the present invention. It is contemplated that one or more of the disclosed actuators can be included within any of these catheters or catheter assemblies.

The following example is provided to illustrate certain particular features and/or embodiments. This example should not be construed to limit the disclosure to the particular features or embodiments described.

EXAMPLE

This example describes methods of fabricating exemplary cylindrical IPMCs and uses thereof.

Cylindrical ionic polymers were fabricated using hot pressing process and the surface electrode of the cylindrical IPMC was inter-digitated. As a result, the resulting data including the bending angle and blocking force of the 2-DOF bending of the cylindrical IPMC with a diameter of 1 mm and a length of 20 mm are presented.

i. Initial FE Analysis

Analysis on the geometry of the cylindrical IPMC and the combination of the input signal were carried out using a 3D FE model. The model was based on the calculations of the ionic migration and diffusion which are directly related to the bending of the IPMC. The cation concentration in the IPMC was calculated using the system of Nernst Planck and Poisson equations:

$$\frac{\partial C}{\partial t} + \nabla \cdot (-D\nabla C - z\mu FC\nabla \phi) = 0, \quad (1)$$

$$-\Delta \phi = \frac{Fp}{\varepsilon}, \quad (2)$$

where C is the cation concentration; D diffusion constant; $\phi$, electric potential; F the Faraday constant; $\mu$ mobility; and $\in$ absolute dielectric constant. In the initial analysis, the local charge density, $\rho$, was coupled to the local stress by using the force relation $$F_x = A\rho^2 + B\rho, \quad (3)$$

where $F_x$ is the body force in the longitudinal direction. The detailed model, including the details about the Navier's equation is described in Pugal et al. (*Journal of Applied Physics*, 103(8): 6, 2008). The equations were implemented in Comsol Multiphysics software package. The main simulation constants are shown in Table I.

TABLE I

SIMULATION CONSTANTS

| Constant | Value | Unit |
|---|---|---|
| Diffusion constant D | 12e−12 | m²/s |
| Dielectric permittivity $\epsilon$ | 2e−3 | F/m |
| Force coupling A | 8e4 | — |
| Force coupling B | 6e7 | — |

The diameter and the length of the actuator were set to be 1 mm and 20 mm, respectively. The 1 mm thickness was chosen due to manufacturing considerations. For a beam-shaped conventional IPMC, the input signal is quite straightforward because it simply bends toward the anode direction. In case of a cylindrical IPMC which have at least four independent electrodes, the input signal can have more combinations to potentially actuate in 8 different directions.

Figure 2:
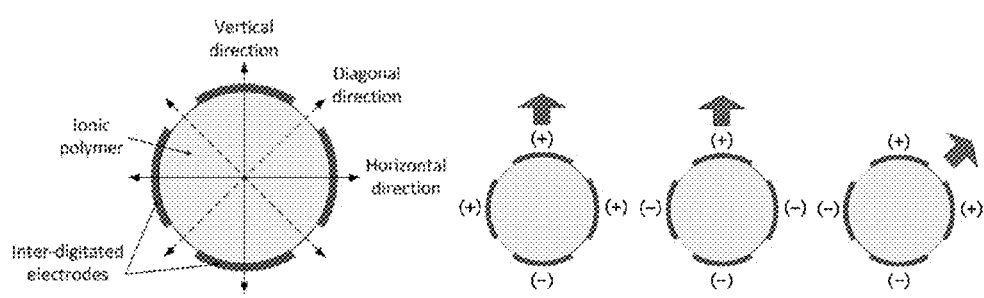
FIG. 2 is a schematic illustrating actuation directions and different actuation schemes for the vertical/horizontal direction as for the diagonal direction.

Illustrated in FIG. 2 are two ways of actuating the cylindrical IPMC in the vertical/horizontal directions—three positive signals and one positive signal. On the other hand, there is only one way to actuate the illustrated cylindrical IPMC in the diagonal direction, which is by applying positive signals to coinciding electrodes.

Figure 3:
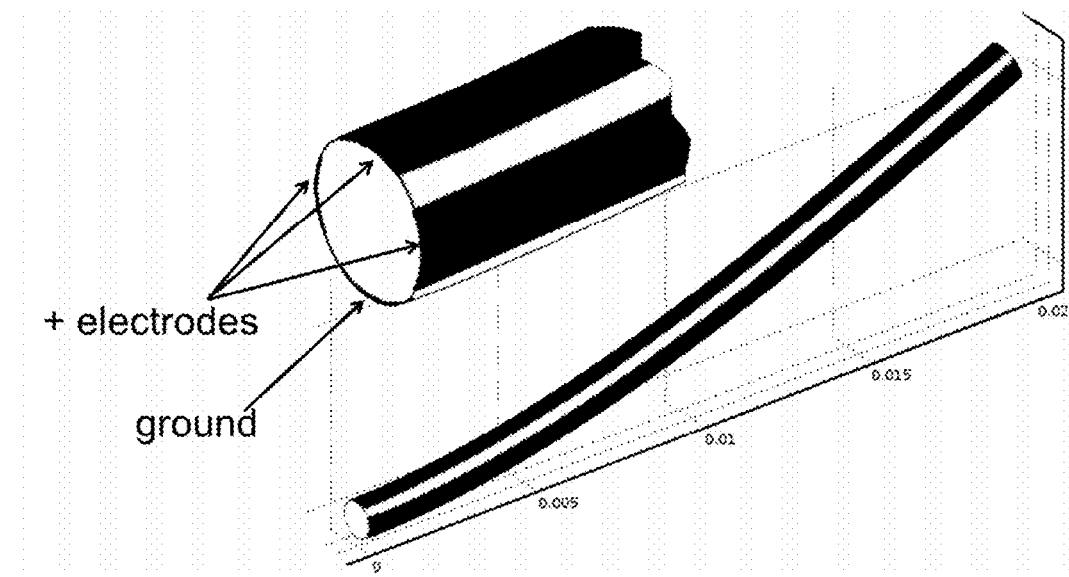
FIG. 3 is schematic illustrating a simulated bending in the vertical/horizontal direction with three plus electrodes.
Figure 4:
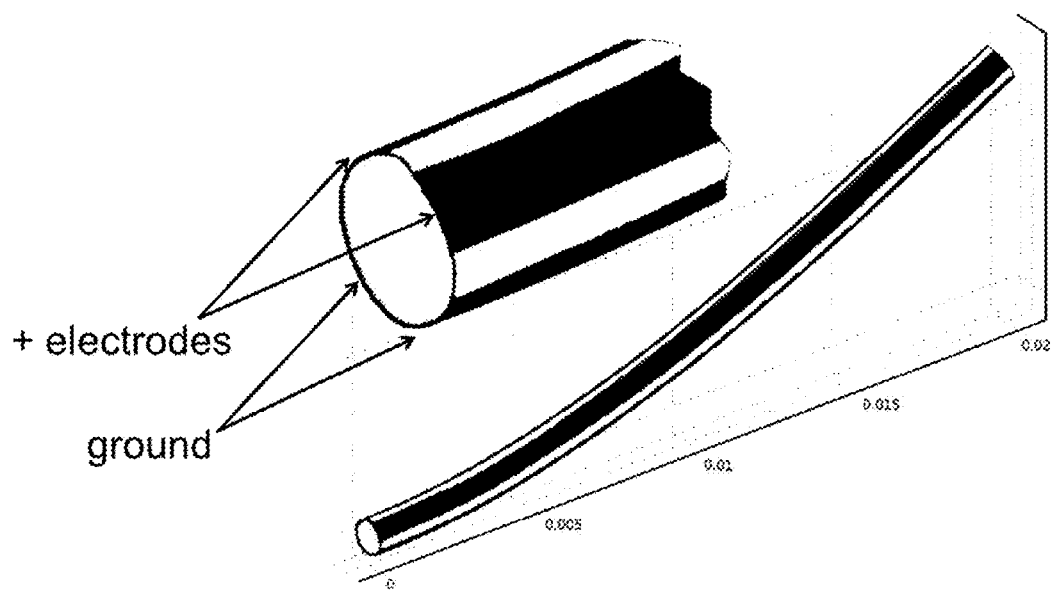
FIG. 4 is a schematic illustrating a simulated bending in the diagonal direction. The solid black portion indicates the positive voltage.
Figure 5:
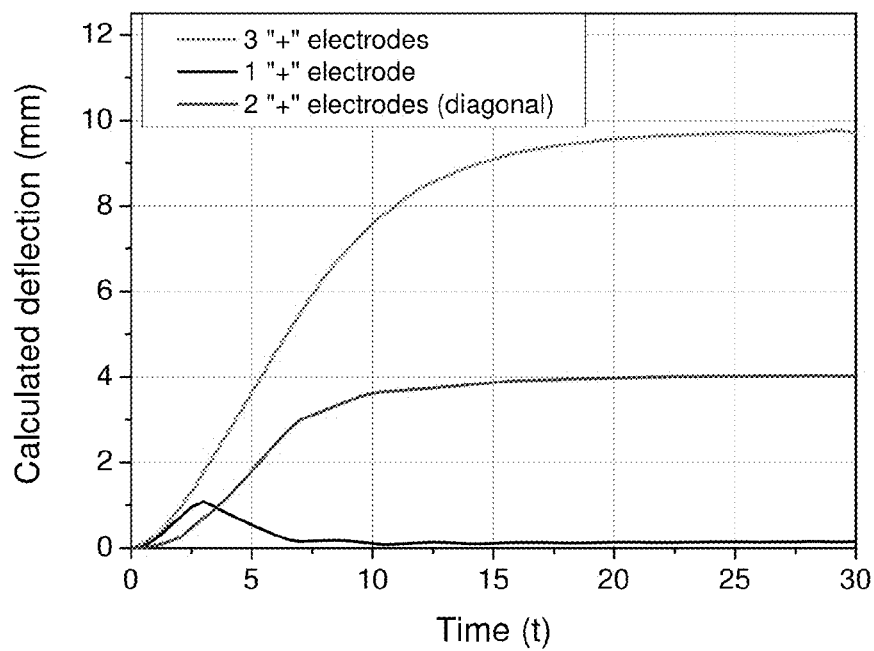
FIG. 5 is a tracing illustrating initial calculation of the bending deflection for different applied signals (see FIG. 2) using the force coupling in Eq. (3). 4V actuation signals were used in this simulation.

A set of simulations were carried out for a cylindrical IPMC. The results showed that the eight directional bending is indeed possible. The model predicted reasonable diagonal bending and the bending in case of three positive signals. It is illustrated in FIGS. 3 and 4. However, the model was not able to estimate the bending in case of one positive signal. The calculation results in case of 4V applied voltage are shown in FIG. 5.

The simulations results were sufficient to move onto next step, namely to fabricate and characterize the cylindrical IPMCs. Thereafter, based on the generated data, the force coupling Eq. (3) was redefined and another set of simulations was carried out. More calculated data are presented in the Results and Discussion Section below.

ii. Fabrication a. Cylindrical IPMC

IPMCs are typically fabricated by chemically depositing platinum electrode layer on the surfaces of a commercially available film-type ionic polymer. In the present study, the cylindrical ionic polymer rods were fabricated in-house. Ionic polymer (Nafion®, Dupont®) beads were hot-pressed in a mold at 3,000 psi for 30 minutes at an elevated temperature of 150° C. (3912, Carver, Inc.). After the polymer was molded with a desired shape, an activation process was carried out before platinum electroless plating process, since the Nafion® beads did not have the cation-exchange properties. The activation process was divided into two steps, hydrolysis and acid conversion.

Hydrolysis: The membrane was hydrolyzed in a solution of KOH at an elevated temperature. After the hydrolysis, the cations of the membrane were in K⁺ form.

Acid conversion: The cations of the hydrolyzed membrane were converted to H⁺ form in a 15% solution of $HNO_3$ at the room temperature for about 4 hours. Platinum electrode layers were deposited on the surface of the activated cylindrical membrane using the typical platinum electroless plating process. Later the cations of the fabricated cylindrical IPMC were exchanged to Li⁺ form in 1 M LiCl solution at the room temperature for 4 hours. All the chemicals were obtained from Sigma-Aldrich®.

b. Inter-Digitated Electrodes

Figure 6:
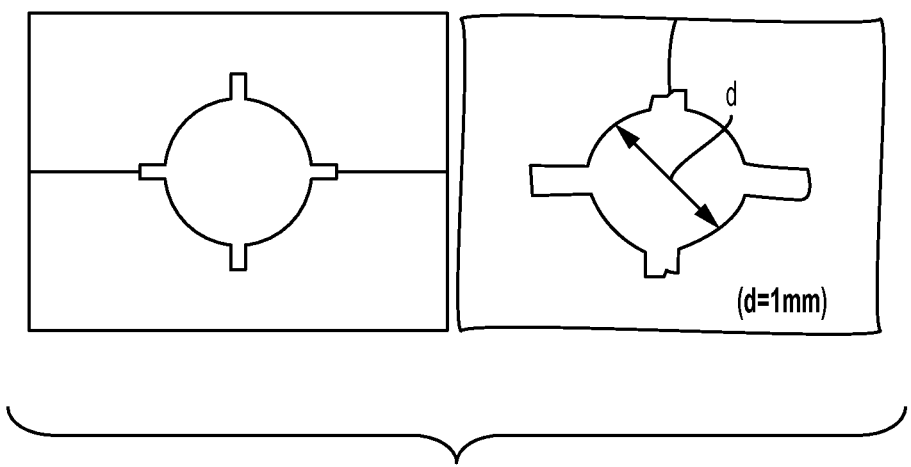
FIG. 6 is a schematic of a cross-sectional view of a mold to make four projections on a cylindrical membrane (left panel) and fabricated membrane having four projections (right panel).
Figure 7:
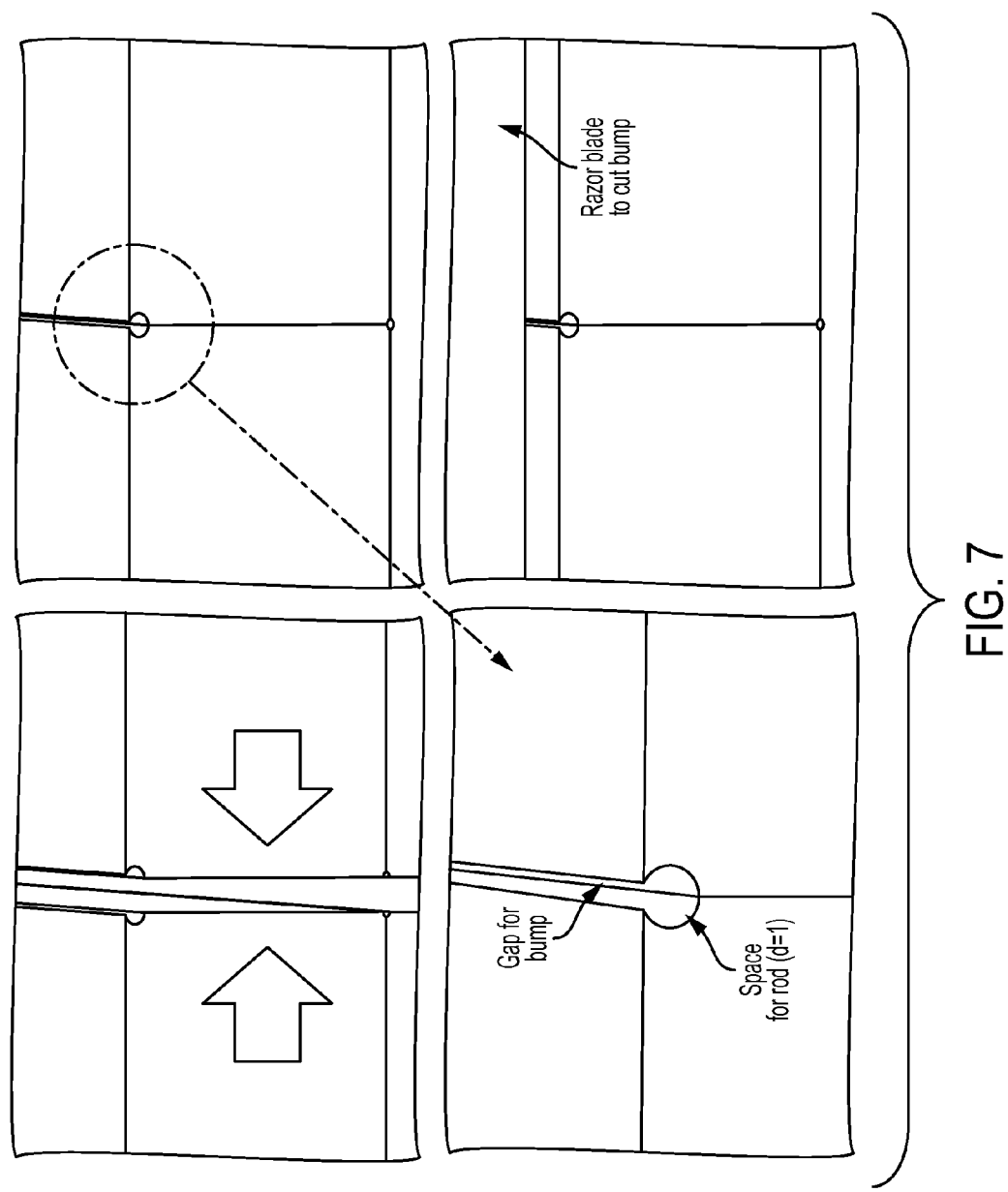
FIG. 7 is a series of digital images of tools and process for removing the projections around the cylindrical IPMC.
Figure 19:
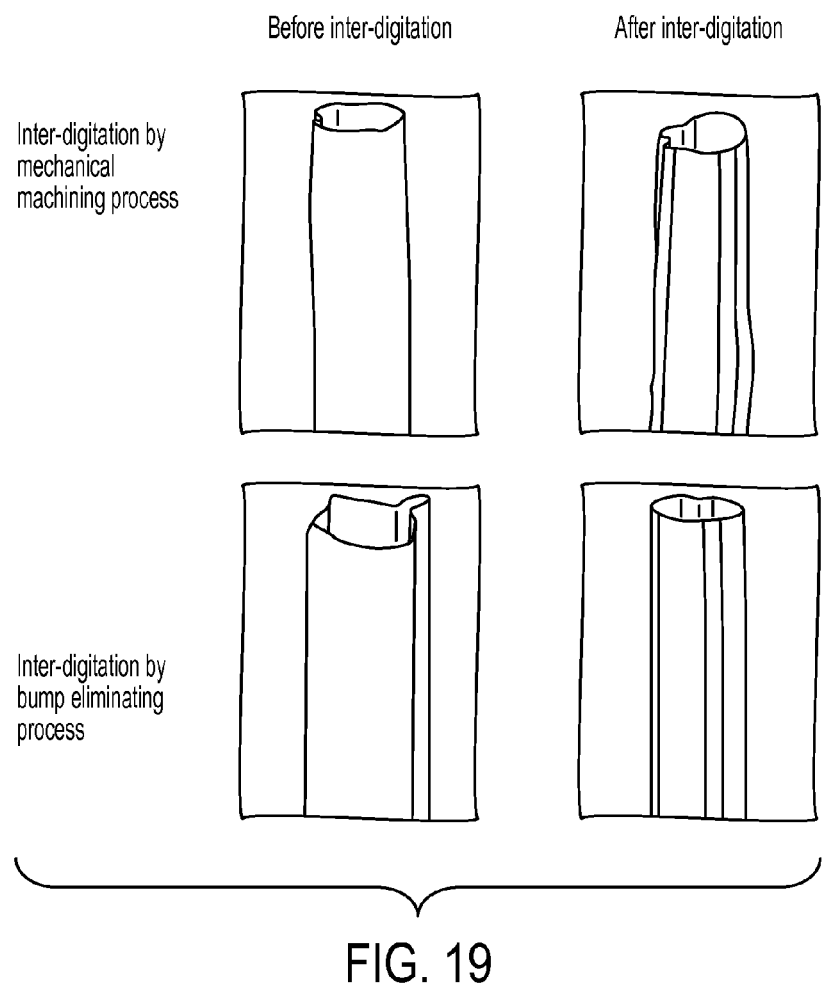
FIG. 19 includes digital images of cylindrical IPMCs before and after inter-digitation

As the inter-digitation of the surface electrode on the cylindrical IPMC with diameter of 1 mm is a quite challenging process, two different methods were tried. Firstly, inter-digitating the surface electrode of the cylindrical IPMC was carried out using a micro-milling machine with the help of a customized sample holder and a digital microscope. However, the vibration during the machining process resulted in damaged polymer rod and rough electrode surface. In order to overcome the drawback of the mechanical machining process, a mold to make the cylindrical membrane with four bumps (projections) of the width of 0.2 mm at every 90° was prepared (see FIG. 6). The inter-digitation of the electrodes was carried out by elimination of the four projections with cutting tools and process as shown in FIG. 7. The comparison in FIG. 19 shows that the projection elimination results in better electrodes compared to the electrodes done with the mechanical machining.

iii. Test Setup a. 2-DOF Actuation

Figure 8:
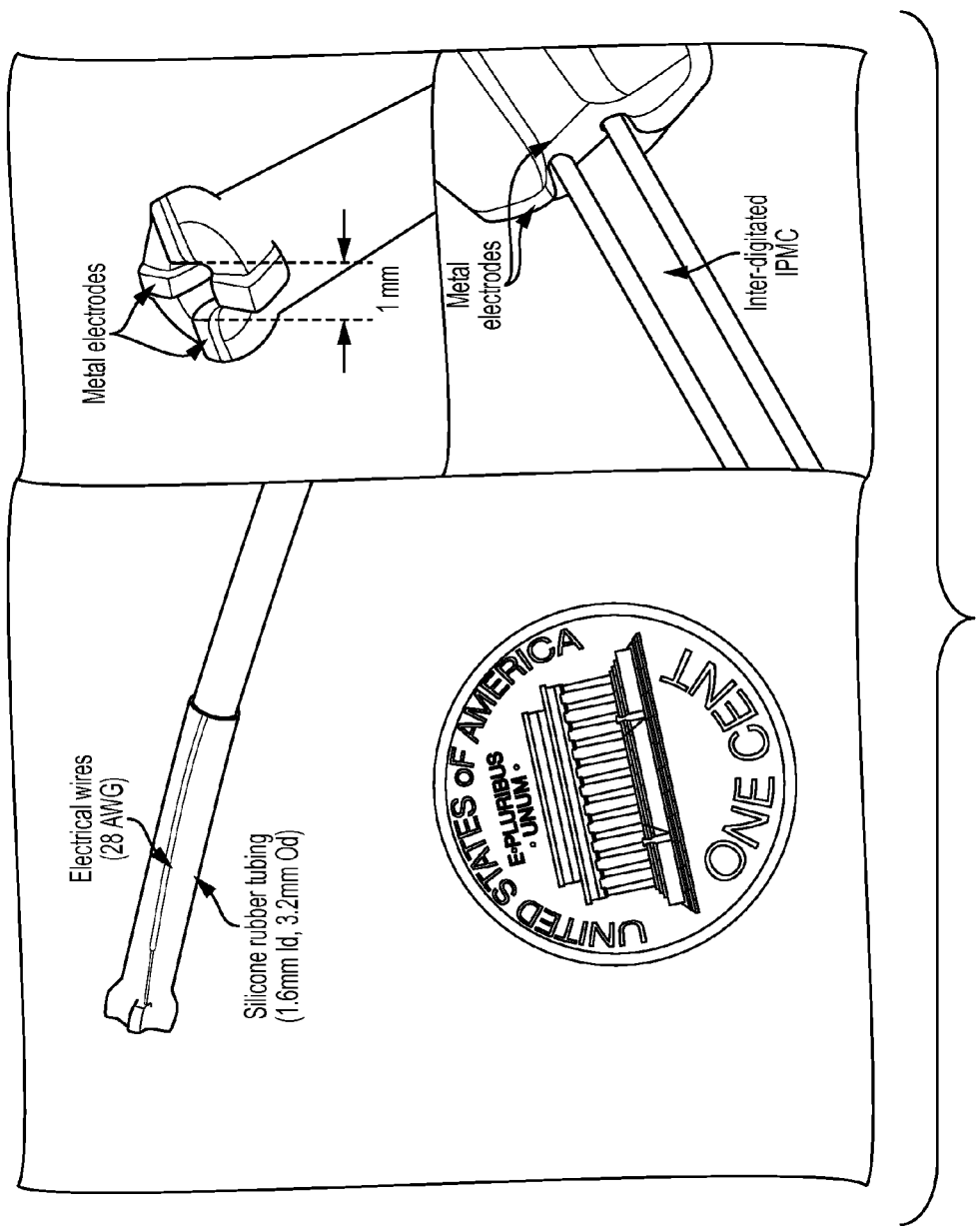
FIG. 8 is a series of digital images of a fabricated contact electrode for the cylindrical IPMCs with 4 inter-digitated electrodes.

The contact electrode that is clamped to the electrodes of the cylindrical IPMC was fabricated using silicon rubber tubing (Inner diameter: 1.6 mm, Outer diameter: 3.2 mm) and electrical wires (28 AWG) as shown in FIG. 8. A customized PLC module (TSB-22R, COMFILE technology) and the direction controller panel shown were made to apply desired control signals to the four inter-digitated electrodes.

b. Electromechanical Properties

Figure 9:
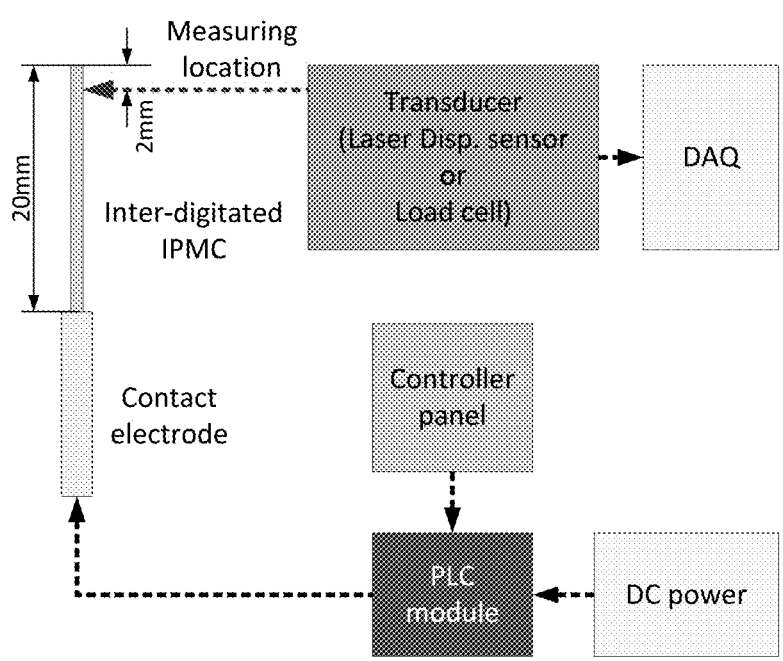
FIG. 9 is a flow diagram illustrating bending deflection measurement setup.

The electromechanical responses such as bending deflection and blocking force of the fabricated cylindrical IPMC were measured using a laser displacement sensor (ILD-1401, Micro-Epsilon) and a load cell (GSO-10, Transducer techniques) with a sample having a diameter of 1 mm and a length of 20 mm. As shown in FIG. 9, the test setup was composed of DAQ (SCB-68, National Instruments), DC power supply (CPS250, Tektronix), as well as the mentioned transducers.

Figure 10:
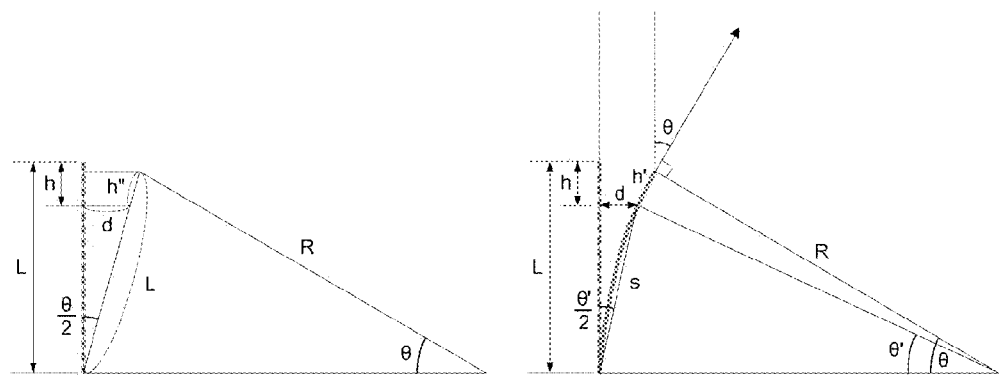
FIG. 10 illustrates geometrical considerations to calculate the bending angle from the bending deflection. Drawing for definition of the parameters is provided in the left panel. Drawing for the approximation of h' is provided in the right panel.

In this study, bending angle of the cylindrical IPMC was acquired by converting the measured bending deflection. In order to convert a bending deflection to a bending angle, it was assumed that the actuator deforms with uniform curvature along the length. Using the geometrical relations shown in FIG. 10 and the following equations, a function of the bending angle $\theta$ in terms of tip deflection $d$ can be derived as expressed in Eq. (10).

$$s = 2R\sin(\theta'/2) \tag{4}$$

$$R = \frac{L}{\theta} \tag{5}$$

$$\theta' = \left(\frac{L-h'}{L}\right)\theta = k\theta \tag{6}$$

$$\sin(\theta'/2) = \frac{d}{s} \tag{7}$$

$$d = \frac{2L}{\theta}\sin^2\left(\frac{\theta'}{2}\right) = \frac{L(1-\cos k\theta)}{\theta} \tag{8}$$

$$h' \cong h'' = \frac{L(\cos(\theta/2)-1)+h}{\cos(\theta/2)} \tag{9}$$

In case of L=20 mm, h=2 mm, $$\theta = 166.5676 \ast (1 - \exp(-0.0444 \ast d)) \tag{10}$$

iii. Results and Discussion

Figure 11:
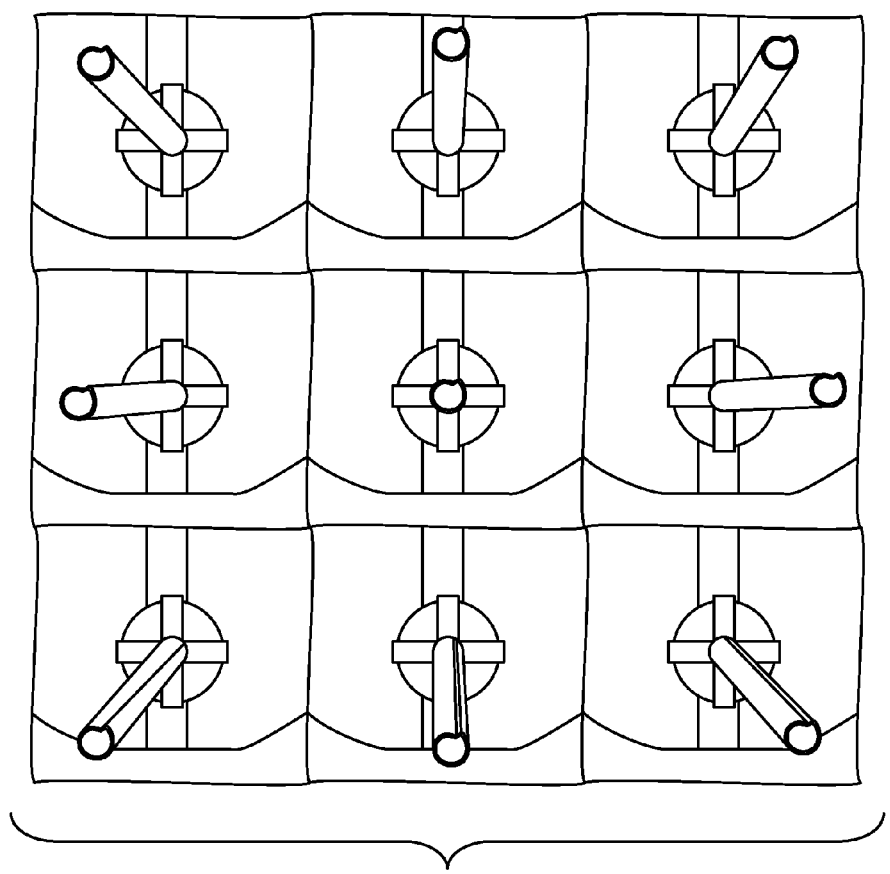
FIG. 11 is a series of digital images illustrating actuation of the cylindrical IPMC in 8-directions.

FIG. 11 shows the actuation of the cylindrical IPMC in 8 directions including vertical/horizontal directions and diagonal directions. The measured bending deflection and converted bending angle of the cylindrical IPMC in the vertical/horizontal direction with applied voltages of 2 to 4V DC are shown in FIGS. 12 and 13.

Figure 12:
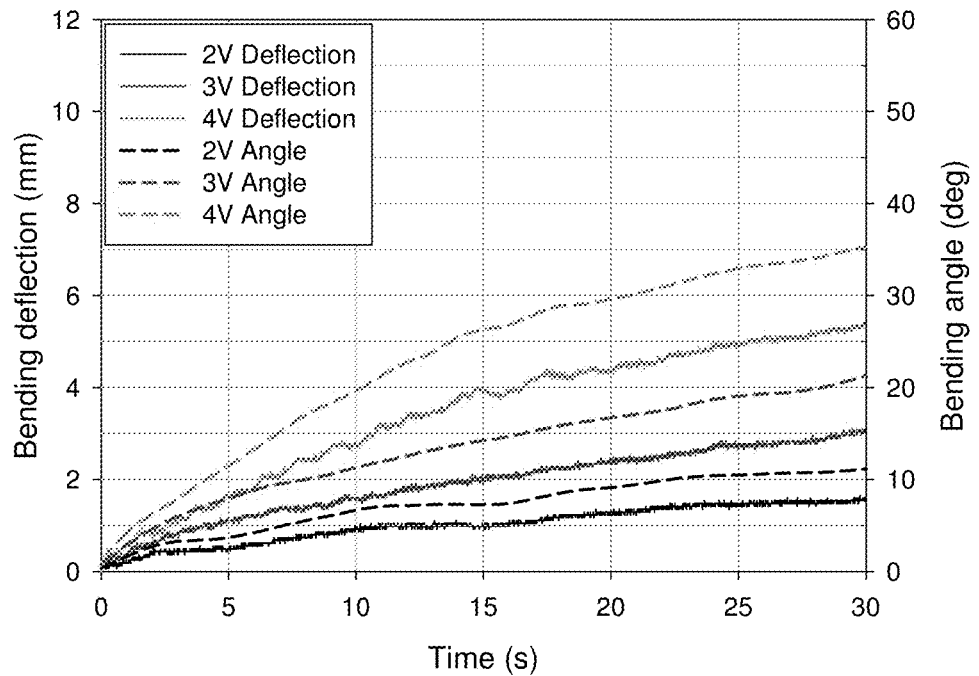
FIG. 12 is a graph bending deflection and bending angle in the vertical/horizontal direction with 3 positive actuation signals.
Figure 13:
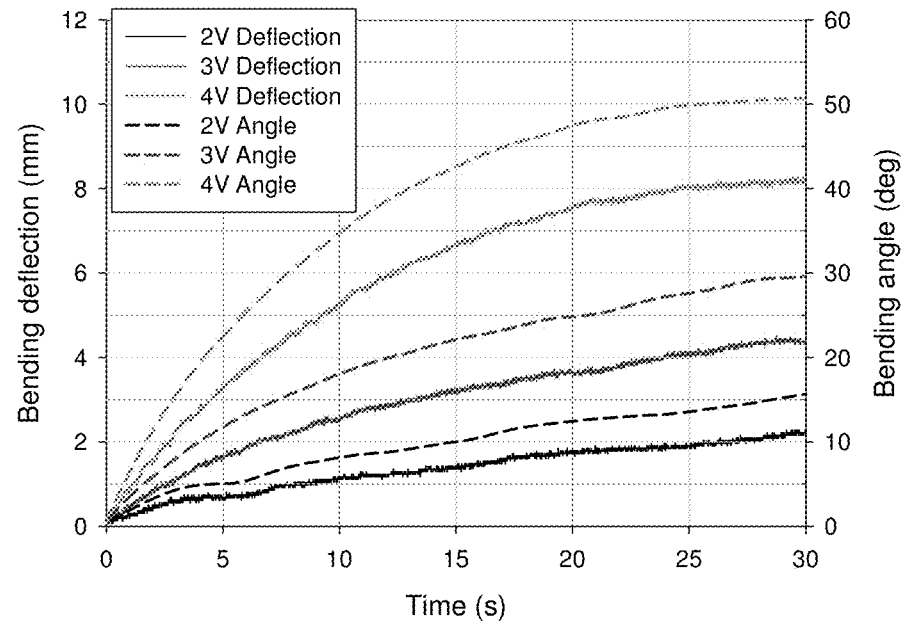
FIG. 13 is a graph illustrating bending deflection and bending angle in the vertical/horizontal direction with 1 positive actuation signal.

FIG. 12 represents the results when the positive signal was applied to three electrodes as discussed above. The bending angles achieved during 30 seconds of actuation were approximately 10°, 20°, and 35° for 2V, 3V, and 4V driving signals, respectively. FIG. 13 shows the results when the positive signal was applied to one electrode. The bending angles achieved in 30 seconds of actuation were approximately 15°, 30°, and 50° for 2V, 3V, and 4V driving signals, respectively. It can be seen that both bending deflection and angle are approximately 50% better in case of applying only one positive signal compared to applying the three positive signals.

Figure 14:
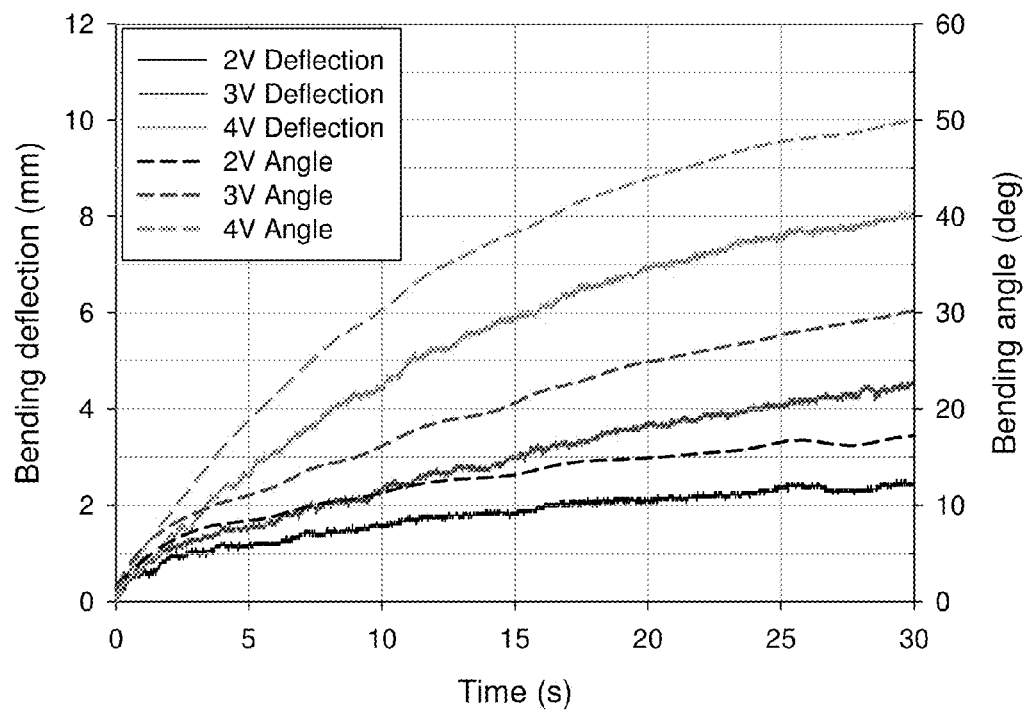
FIG. 14 is a graph illustrating bending deflection and bending angle in the diagonal direction with 2 positive actuation signals.

FIG. 14 shows the measured bending deflection and the converted bending angle of the cylindrical IPMC in diagonal direction with applied voltages of 2 to 4V DC. A positive signal was applied to the 2 electrodes as also discussed above. The maximum amplitude of bending in the diagonal direction is similar to that of the one positive electrode case in the vertical/horizontal direction.

Figure 15:
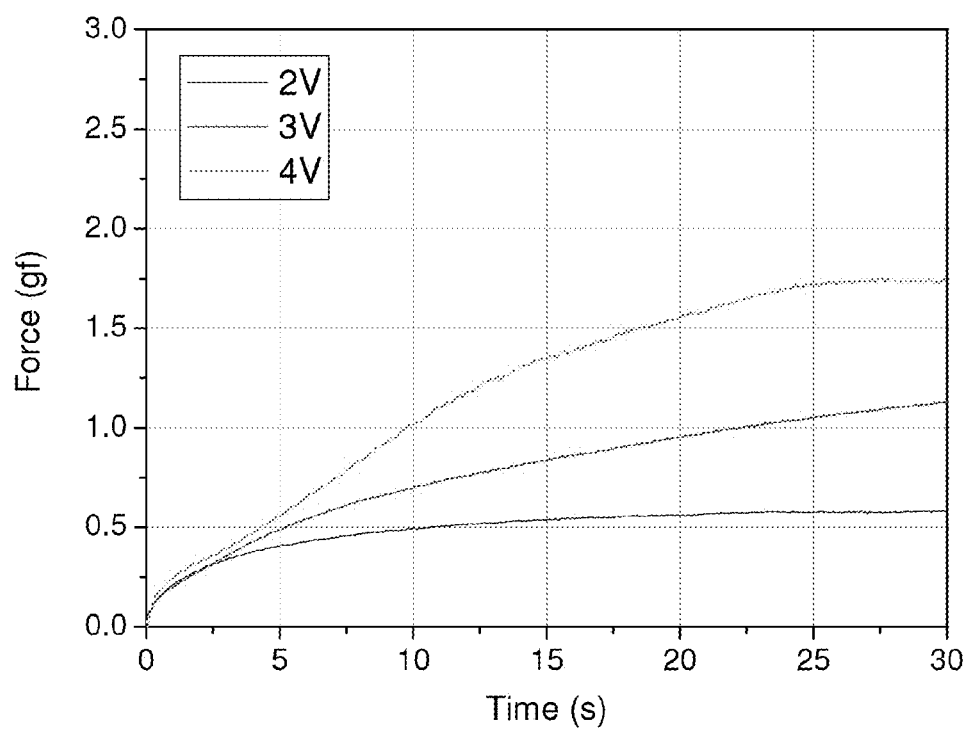
FIG. 15 is a graph illustrating blocking force in the vertical/horizontal direction with 3 positive actuation signals.
Figure 16:
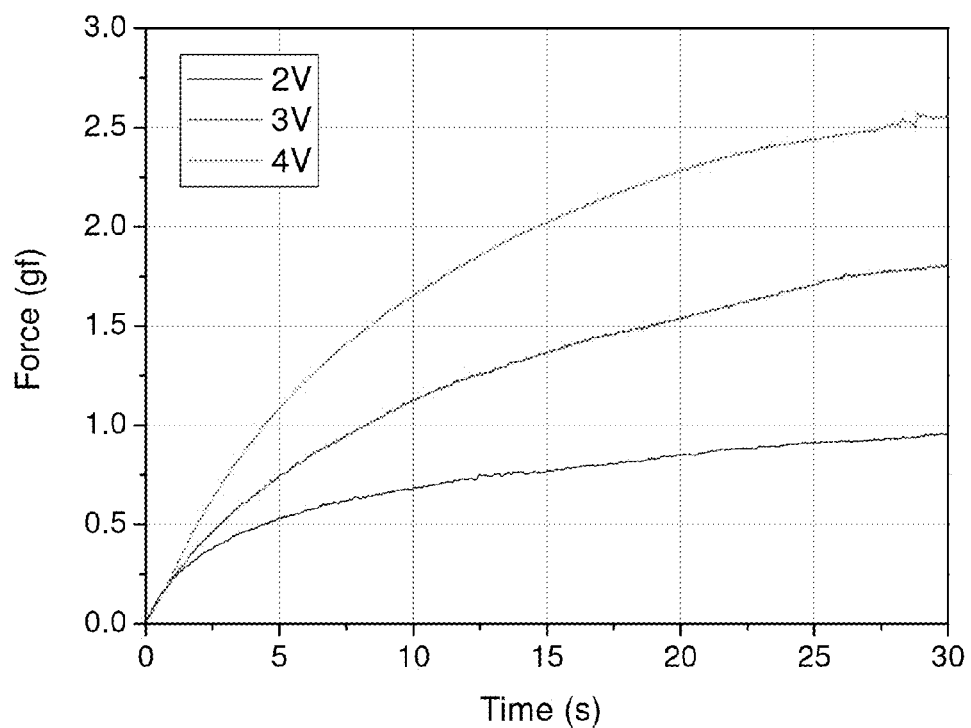
FIG. 16 is a graph illustrating blocking force in the vertical/horizontal direction with 1 positive actuation signal.
Figure 17:
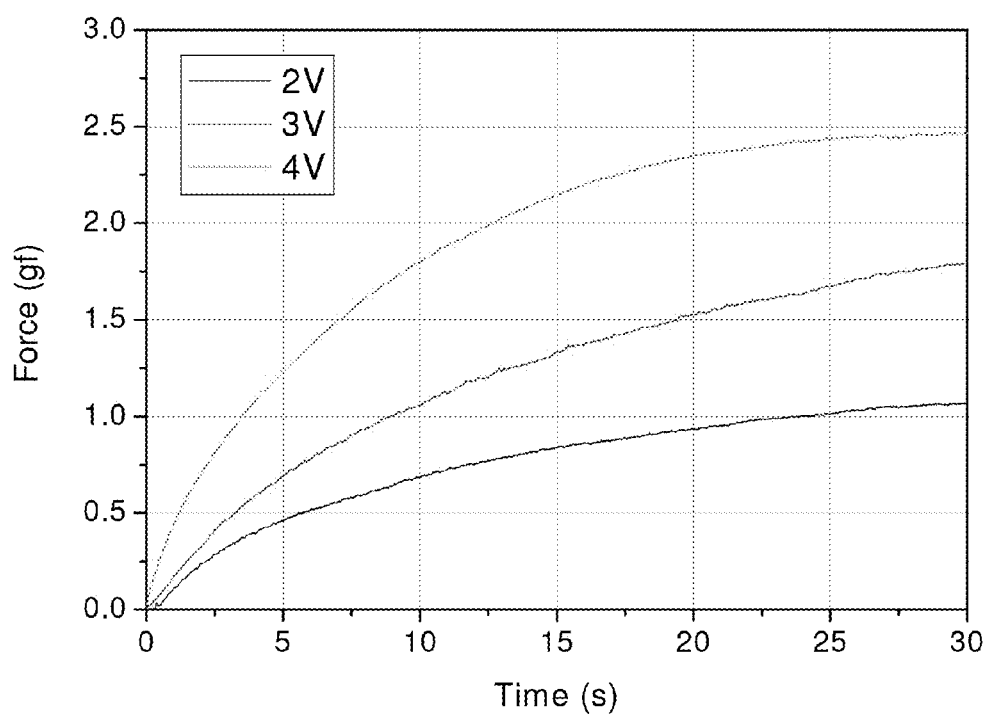
FIG. 17 is a graph illustrating blocking force in the diagonal direction with 2 positive actuation signals.

Blocking force measured with driving signals from 2 to 4V in the vertical/horizontal direction and diagonal direction are shown in FIGS. 15-17, respectively. Similar tendency to the results of bending angle (deflection) was observed—namely, the three positive actuation signals resulted in significantly lower output than that of the one positive actuation signal. Also, measured force of the one actuation signal case is similar to the diagonal force measurement.

It is noted that the measured current during the actuation corresponds to the deflection and force output, i.e. in case of three positive actuation signals, the measured current was the lowest and it was approximately the same in case of the one positive actuation signal and diagonal bending with two positive actuation signals.

When comparing the graphs in FIGS. 12 and 13 (as well as in FIGS. 15 and 16), it can be seen that the one plus electrode results in better deflection (and force) than three plus electrodes. The initial model presented herein did not predict almost any bending in case of one plus electrode. However, the data suggest that the anode of IPMCs contributes more in terms of creating the bending actuation. In view of this, the force coupling Eq. (3) was modified. After conducting a parametric study, special terms were added to separate the anode and cathode force couplings, resulting in the following formulation $$F_{x_{mod}} = A\frac{\text{sgn}(\rho)+1}{2}\rho^2 - B\frac{\text{sgn}(\rho)-1}{2}\rho. \tag{11}$$

Figure 18:
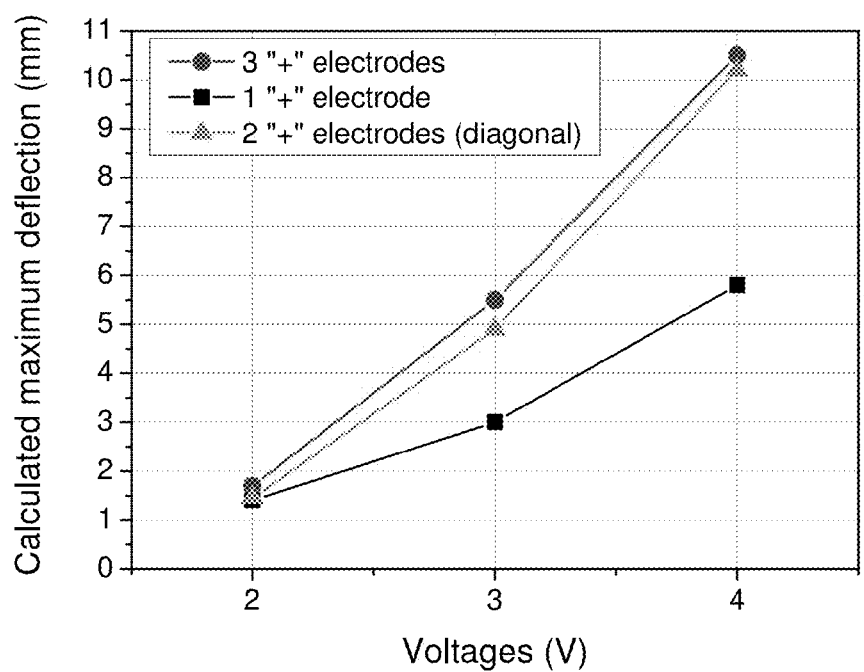
FIG. 18 is a graph illustrating maximum displacement d simulated with the time dependent FE model for different actuation signals and voltages.

Here the quadratic term applies only when $\rho$ is positive and the linear terms when $\rho$ is negative. The deflection simulations, based on the same FE model presented herein, were run with the new body force variable $F_{x_{mod}}$. The maximum deflections for each signal mode for three different voltages are shown in FIG. 18. It can be seen that the enhanced model correctly predicts that the one positive signal results better actuation performance than three positive actuation signals.

An effective fabrication method for cylindrical IPMC actuators for 2-DOF bending was successfully developed. Finite element analysis was used before fabrication to ensure the actuation capabilities of the cylindrical IPMC. A rod shaped IPMC with 4 inter-digitated electrodes was made and the actuation capability in 4 directions was demonstrated. Bending angles up to 50° were achieved. Furthermore, the finite element model that was used for initial calculations was developed further based on the generated data. Due to the electrode configuration and the shape of the IPMC, it was found that the anode and cathode areas contribute differently to the bending.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of fabricating a multiple degree of freedom actuator with inter-digitated electrodes, comprising:
   molding an electroactive polymer membrane so that a plurality of projections are formed around a cross section of an outer surface of the polymer membrane;
   depositing a metal electrode layer onto the outer surface of the molded membrane; and
   removing the plurality of projections on the outer surface on the molded membrane, thereby forming a multiple degree of freedom actuator with a plurality of inter-digitated electrodes.

2. The method of claim 1, wherein the plurality of projections are approximately 0.2 mm in width and are position at approximately 90° of each other.

3. The method of claim 1, wherein each projection extends longitudinally along the molded membrane.

4. The method of claim 1, wherein the removing the plurality of projections is by use of a cutting tool.

5. The method of claim 1, wherein the electroactive polymer comprises an ionic polymer metal composite (IPMC).

6. The method of claim 1, wherein the method is used to form an actuator with 4 inter-digitated electrodes.

7. The method of claim 1, wherein the actuator is for a catheter.

8. The method of claim 1, wherein the method does not comprise mechanical or laser machining.

9. An actuator formed by the method of claim 1.

10. The actuator of claim 9, wherein the actuator is cylindrical in shape.

11. The actuator of claim 10, wherein the actuator comprises ionic polymer metal composite (IPMC) and 4 inter-digitated electrodes.

12. The actuator of claim 11, wherein the actuator has actuation capability in 4 directions.

13. The actuator of claim 12, wherein the actuator has capability of bending to angles up to 50°.

14. The actuator of claim 13, wherein the actuator has a cross section of about 1 mm.

15. The actuator of claim 14, wherein the actuator is about 20 mm length.

16. The actuator of claim 10, wherein the actuator further comprises a contact electrode.

17. The actuator of claim 16, wherein the contact electrode is connected to the inter-digitated electrodes by a composition comprising silicone rubber.

18. A catheter comprising one or more actuators of claim 17.

* * * * *